(12) United States Patent
Koehler et al.

(10) Patent No.: US 9,488,574 B2
(45) Date of Patent: Nov. 8, 2016

(54) DEVICE FOR IMAGING THE INTERIOR OF AN OPTICALLY TURBID MEDIUM AND RECEPTACLE UNIT FOR SUCH A DEVICE

(75) Inventors: Thomas Koehler, Norderstedt (DE); Tim Nielsen, Hamburg (DE); Bernhard Brendel, Hamburg (DE); Andy Ziegler, Kelburn/Wellington (NZ); Ronny Ziegler, Hamburg (DE); Levinus Pieter Bakker, Shanghai (CN); Martinus Bernardus Van Der Mark, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1756 days.

(21) Appl. No.: 12/682,939

(22) PCT Filed: Oct. 13, 2008

(86) PCT No.: PCT/IB2008/054197
§ 371 (c)(1),
(2), (4) Date: Apr. 14, 2010

(87) PCT Pub. No.: WO2009/050633
PCT Pub. Date: Apr. 23, 2009

(65) Prior Publication Data
US 2010/0238441 A1    Sep. 23, 2010

(30) Foreign Application Priority Data

Oct. 19, 2007  (EP) .................................... 07118848

(51) Int. Cl.
*G01N 21/47* (2006.01)
*A61B 5/00* (2006.01)
*G01N 21/17* (2006.01)

(52) U.S. Cl.
CPC ......... *G01N 21/4795* (2013.01); *A61B 5/0091* (2013.01); *A61B 5/4312* (2013.01); *A61B 5/0073* (2013.01); *A61B 2562/146* (2013.01); *G01N 2021/1787* (2013.01); *G01N 2201/0826* (2013.01); *G01N 2201/0833* (2013.01)

(58) Field of Classification Search
USPC .................................................. 600/473–476
See application file for complete search history.

(56) References Cited

U.S. PATENT DOCUMENTS 4,075,883 A * 2/1978 Glover ........................... 73/607
5,408,093 A    4/1995 Ito et al.
(Continued)

FOREIGN PATENT DOCUMENTS

WO       0056206 A1    9/2000
WO    2007057798 A2    5/2007

*Primary Examiner* — Rochelle Turchen

(57) ABSTRACT

A device (1) for imaging the interior of an optically turbid medium is provided. The device comprises a receptacle (3; 103) structured to accommodate an optically turbid medium for examination and an optically matching medium filling a space between an inner surface (6; 106) of the receptacle (3; 103) and the optically turbid medium. The device comprises at least one light source generating light to be coupled into the receptacle (3; 103) and at least one detector for detecting light emanating from the receptacle (3; 103). A coupling surface (10; 110) optically coupled to the inner surface (6; 106) of the receptacle and a coupling member (11; 111) optically coupled to the light source and the detector are provided. The coupling surface (10; 110) and the coupling member (11; 111) are movable to a plurality of different positions relative to each other and structured to establish an optical connection from the light source to the inner surface (6; 106) of the receptacle and from the inner surface (6; 106) of the receptacle to the at least one detector in the plurality of different positions.

10 Claims, 2 Drawing Sheets

(56) References Cited

U.S. PATENT DOCUMENTS

| | | |
|---|---|---|
| 6,029,077 A | 2/2000 | Wake et al. |
| 6,100,520 A | 8/2000 | Wake et al. |
| 6,345,194 B1 | 2/2002 | Nelson et al. |
| 6,480,281 B1 * | 11/2002 | Van Der Mark et al. .... 356/432 |
| 6,795,195 B1 | 9/2004 | Barbour et al. |
| 2002/0045833 A1 | 4/2002 | Wake et al. |
| 2002/0100864 A1 | 8/2002 | Wake |
| 2004/0171938 A1 | 9/2004 | Grable |

* cited by examiner

DEVICE FOR IMAGING THE INTERIOR OF AN OPTICALLY TURBID MEDIUM AND RECEPTACLE UNIT FOR SUCH A DEVICE

FIELD OF INVENTION

The present invention relates to a device for imaging the interior of an optically turbid medium and to a receptacle unit for such a device. More specifically, the present invention relates to a device for imaging the interior of an optically turbid medium and to a receptacle unit for such a device which comprise a receptacle structured to accommodate an optically turbid medium to be examined and to accommodate an optically matching fluid filling a space between an inner surface of the receptacle and the optically turbid medium.

BACKGROUND OF THE INVENTION

In the context of the present application, the term turbid medium is to be understood to mean a substance consisting of a material having a high light scattering coefficient, such as for example an Intralipid solution or biological tissue. Further, light is to be understood to mean electromagnetic radiation of a wavelength in the range from 400 nm to 1400 nm. The term "an element is optically coupled to another element" means that at least one light path is formed along which light is transmitted between the elements. The term "optical properties" covers the reduced scattering coefficient $\mu'_s$ and the absorption coefficient $\mu_a$. Furthermore, "matching optical properties" is to be understood as having a similar reduced scattering coefficient $\mu'_s$ and a similar absorption coefficient $\mu_a$.

In recent years, several methods and devices for examining turbid media, e.g. female breast tissue, have been developed. In particular, new devices for detection and analysis of breast cancer have been developed and existing technologies have been improved. Several types of devices for imaging the interior of a turbid medium by use of light have been developed. Examples for such devices are mammography devices and devices for examining other parts of human or animal bodies. A prominent example for a method for imaging the interior of a turbid medium is Diffuse Optical Tomography (DOT). In particular, such devices are intended for the localization of inhomogeneities in in vivo breast tissue of a part of a breast of a female human body. A malignant tumor is an example for such an inhomogeneity. The devices are intended to detect such inhomogeneities when they are still small, so that for example carcinomas can be detected at an early stage. A particular advantage of such devices is that the patient does not have to be exposed to the risks of examination by means of ionizing radiation, as e.g. X-rays.

New approaches for further enhancing the accuracy of methods for detecting breast cancer by use of light have been made. For example, a fluorescent dye has been developed which can be injected into the body and will accumulate in cancer cells. If this fluorescent dye then becomes excited with light of a suitable wavelength, the locally emitted light can be detected. Based on the emitted light, size and localization of carcinoma can be determined. Thus a powerful method for detection and localization of breast cancer is provided.

WO 00/56206 A1 discloses a device for imaging the interior of a turbid medium by using a light source to irradiate the turbid medium and photodetectors for measuring a part of the light transported through the turbid medium. A control unit is provided for reconstructing an interior of the turbid medium on the basis of the measured intensities. The disclosed device is particularly adapted for examining female breasts. In order to allow the examination of the turbid medium, the device is provided with a receptacle enclosing a measuring volume and arranged to receive the turbid medium. The light used for examining the turbid medium has to be transmitted from the light source to the turbid medium and from the turbid medium to the photodetectors. Due to different sizes of the turbid media to be examined, the size of the receptacle for receiving the turbid medium does not perfectly match the size of the turbid medium, i.e. a space remains between the receptacle and the turbid medium. A number of light paths coupling to the light source and a number of light paths coupling to photodetectors are distributed across the wall of the receptacle, i.e. ends of optical fibers acting as light guides are connected to the wall of the receptacle. The space between the receptacle and the turbid medium is filled with a so-called optically matching fluid as an optically matching medium. The optically matching fluid provides optical coupling between the part of the turbid medium to be imaged and the light guides connecting to the light source and the photodetectors, respectively. Further, the optically matching fluid is intended to prevent optical short-cutting between the light source and the photodetectors, i.e. light transmitted from the light source to the photodetectors without being transmitted through the turbid medium. The optically matching fluid counteracts boundary effects in the reconstructed image which are caused by the difference in optical contrast between the interior of the turbid medium in the receptacle and the remaining space in the receptacle. In the disclosed device, the positions of the photodetectors and of the light source relative to the receptacle, and thus relative to the examined turbid medium, are fixed. The light source subsequently irradiates the turbid medium and the photodetectors measure a part of the light transmitted through the turbid medium. A plurality of such measurements are performed and, based on the results of the measurements, the control unit reconstructs the image of the examined turbid medium.

According to the prior art implementation of such a device for imaging the interior of a turbid medium, the light enters and leaves the receptacle via fibers which are at fixed locations. In order to perform a complete examination of the turbid medium, the light has to be subsequently directed to the turbid medium from different directions and the corresponding signals of the detectors have to be detected. Directing light through the different fibers for generating a complete image of the examined turbid medium requires a large, heavy, and expensive fiber switch which makes the overall system design expensive. Further, in the known implementation, due to the switching of the different fibers, the distance between the end at the receptacle side of the fiber connecting to the light source and the end at the receptacle side of a fiber connecting to a particular detector varies during the scan. Thus, during a scan, the end of the corresponding fiber of each detector is sometimes very close to the end of the fiber connecting to the light source and sometimes far away from it. As a consequence, the strength of the signal received by a particular detector varies over a large range. In order to cope with this situation, the detectors have to cope with a large dynamic range of received signal strengths which makes the required detectors expensive and difficult to calibrate. Further, in use in diffuse optical fluorescence tomography using a fluorescent contrast agent the signal levels are very low, especially when the optical path through the tissue is long. This necessitates the use of sensitive low-noise detectors which are expensive. Since a large number of detectors is required in the known devices for providing the required image—for example about 250 detectors in a device known to the applicant—achieving a high accuracy image becomes expensive.

SUMMARY OF THE INVENTION

Thus, it is the object of the present invention to maintain the advantages which are achieved by using a receptacle filled with an optically matching medium while reducing the costs for the switching of fibers and for signal detection. Further, calibration and maintenance of the detectors are simplified and adaptation of the device to turbid media of different sizes are allowed.

This object is solved by a device for imaging the interior of a turbid medium according to claim 1. The device comprises a receptacle structured to accommodate an optically turbid medium to be examined. The receptacle is structured to accommodate an optically matching medium filling a space between an inner surface of the receptacle and the optically turbid medium. The device further comprises at least one light source generating light to be coupled into the receptacle and at least one detector for detecting light emanating from the receptacle. A coupling surface is optically coupled to the inner surface of the receptacle and a coupling member is optically coupled to the light source and the detector. The coupling surface and the coupling member are movable to a plurality of different positions relative to each other. The coupling surface and the coupling member are structured such that they establish an optical connection from the light source to the inner surface of the receptacle and from the inner surface of the receptacle to the at least one detector in the plurality of different positions.

Since the receptacle accommodating the turbid medium can be filled with an optically matching medium, such as for example an optically matching fluid, boundary effects can be reliably suppressed. Since the coupling surface and the coupling member are movable relative to each other and establish an optical connection in the plurality of different positions, coupling of light from the light source to the receptacle, and thus to the turbid medium, and from the turbid medium and the receptacle to the detector can be switched easily without the necessity for a complicated fiber switch. The number of optical fibers is reduced and the dynamic range of the signals at the detectors is reduced. Further, due to the provision of the coupling surface and the corresponding coupling member, the part of the device comprising the receptacle and the coupling surface can be easily changed. Thus, the device can be easily adapted to turbid media of different sizes.

Preferably, the coupling member is rotatably movable relative to the coupling surface about a rotational axis of symmetry. In this case, many different measurement positions can be realized during a scan without changing the distance between the source and the detector. Thus, calibration of the detector is facilitated and the detector does not have to cope with a large dynamic range of received signal strengths.

Preferably, the coupling member is further linearly movable in the direction of the axis of symmetry. Thus, a large number of different positions for injection of light into the receptacle and a large number of different positions for light paths connecting to detectors can be realized with a reduced number of detectors.

According to an aspect, the coupling surface has a cylindrical shape. In this case, replacement of the part comprising the receptacle and the coupling surface is facilitated. Further, the light source and the detectors, or light guides connecting to the light source and to the detectors, can be arranged on a ring or on a part of a ring which can rotate around the coupling surface. Thus, the device can be realized in a simplified way and thus more cost-effective. Further, many different measurement positions can be realized during a scan without changing the distance between the source and the detector. Thus, calibration of the detector is facilitated and the detector does not have to cope with a large dynamic range of received signal strengths.

If the inner surface of the receptacle is coupled to the coupling surface by means of light guiding fibers, the shape of the coupling surface can be relatively freely designed. This is particularly advantageous when a part of the device comprising the receptacle and the coupling surface is intended to be regularly exchanged or replaced.

According to an aspect, the coupling surface is formed by an outer surface of the receptacle facing away from the turbid medium to be examined. With this feature, the device can be realized in a space-saving manner. An exchangeable receptacle can be advantageously realized.

If the receptacle is made from a material having optical properties similar to the optical properties of the turbid medium to be examined, i.e. matching optical properties, the optical connection between the light source and the turbid medium and between the turbid medium and the detector can be established via the material of the receptacle in a plurality of orientations. Thus, the orientation of the coupling member with respect to the coupling surface is not limited to a restricted number of specific orientations.

Preferably, an optically matching fluid is provided between the coupling surface and the coupling member. In this case, although relative movement is enabled between the coupling surface and the coupling member, the quality of optical coupling can be kept at a high level and boundary effects can be suppressed.

According to a further aspect, the device comprises a receptacle unit comprising the receptacle and the coupling surface. The receptacle unit is removable from the device. As a result, the device can be easily adapted to different sizes of turbid media to be examined such that a high accuracy can be achieved for different sizes of turbid media. Preferably, the device is a medical image acquisition device.

The object is further solved by a receptacle unit according to claim 11. A receptacle unit for a device for imaging the interior of an optically turbid medium comprises a receptacle structured to accommodate an optically turbid medium for examination. The receptacle is structured to accommodate an optically matching fluid filling a space between an inner surface of the receptacle and the optically turbid medium. Further, the receptacle unit comprises a coupling surface optically coupled to the inner surface of the receptacle for coupling light from a light source into the receptacle and for coupling light emanating from the receptacle to a detector via a coupling member optically coupled to the light source and the detector. The receptacle unit is structured such that it is attachable to and detachable from the device for imaging the interior of an optically turbid medium. The coupling surface is structured such that, after mounting in the device, light can be coupled from the light source to the receptacle and from the receptacle to the detector in a plurality of orientations of the coupling surface with respect to the coupling member.

Since the receptacle accommodating the turbid medium can be filled with an optically matching medium, such as for example an optically matching fluid, boundary effects can be reliably suppressed. Since the receptacle unit comprises a coupling surface optically coupled to the inner surface of the receptacle, coupling of light from the light source to the receptacle and from the receptacle to the detector can be switched easily without the necessity for a complicated fiber switch. Further, due to the receptacle unit being structured such that it is attachable to and detachable from the device for imaging the interior of an optically turbid medium, the receptacle unit can be easily exchanged. Thus, the device can be easily adapted to turbid media of different sizes.

BRIEF DESCRIPTION OF THE DRAWINGS

Further features and advantages of the present invention will arise from the detailed description of embodiments with reference to the enclosed drawings.

DETAILED DESCRIPTION OF EMBODIMENTS

Figure 1:
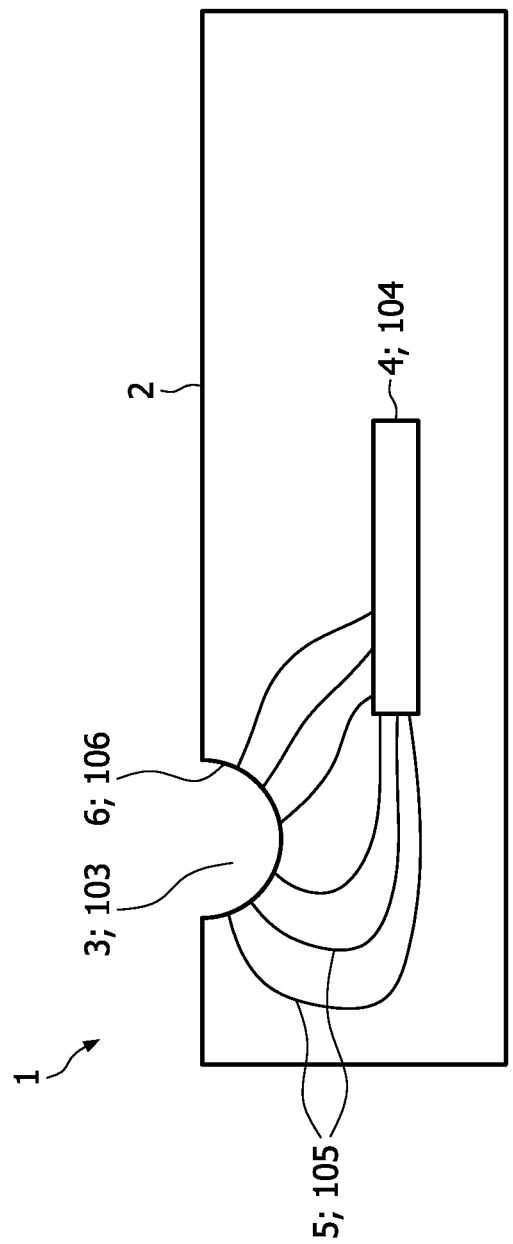
FIG. 1 shows a schematic representation of a device for imaging the interior of an optically turbid medium.

First, the general construction of the device for imaging the interior of an optically turbid medium will be described with reference to FIG. 1. The device according to the embodiments is a device for diffuse optical tomography (DOT) for in vivo examination of biological tissue, in particular for mammography.

The device according to the embodiments uses a laser having a wavelength in the near infrared (NIR) as a light source. In principle, the device 1 operates similar to the device for imaging the interior of a turbid medium described above with respect to the prior art. However, as will be described below, the device differs in the construction of the receptacle, in the arrangement of the light source and the detectors, and in the realization of the light paths between the light source and the receptacle and between the receptacle and the detectors, respectively. As can be seen in FIG. 1, the device 1 comprises a cradle 2 on which a person is placed for examination. A receptacle 3; 103 is attached to the cradle 2 for receiving a turbid medium to be examined, which in the present embodiments is a female human breast. The receptacle 3; 103 has a cup-like shape which is closed at the bottom and has an opening at the upper side. The interior of the receptacle 3; 103 is formed as a cavity. For examination, the person is placed on the cradle 2 and the breast to be examined is placed in the receptacle 3; 103 such that it freely hangs in the receptacle 3; 103. As only schematically indicated in FIG. 1, the inner surface of the receptacle is connected to a measurement system 4; 104 by means of light guides 5; 105. The structure of this optical connection will be described further below with respect to the specific embodiments. The optical connection is established such that the turbid medium located in the receptacle 3; 103 can be illuminated with light from a light source (not shown) and such that light from the turbid medium can be transmitted to detectors (not shown) arranged in the measurement system 4; 104 via the light guides 5; 105. Based on the signals received by the detectors, an image of the interior of the turbid medium is reconstructed. In the schematic representation the light source and the detectors are arranged in the measurement system 4; 104. However, the light source and the detectors may also be arranged at other positions and electrically connected to the measurement system 4; 104.

The size of the receptacle 3; 103 is such that a space remains between the inner surface 6; 106 of the receptacle 3; 103 and the turbid medium. For examination, this space is filled with an optically matching medium which serves to provide optical coupling between the turbid medium to be imaged and the inner surface 6; 106 of the receptacle 3; 103. The optically matching medium further serves to prevent optical short-cutting between the light guides coming from the light source and the light guides coupling to the detectors. Furthermore, the optically matching medium serves to counteract boundary effects in the reconstructed image which are caused by the difference in optical contrast between the interior of the turbid medium and the remaining space in the receptacle 3; 103.

First Embodiment

Figure 2:
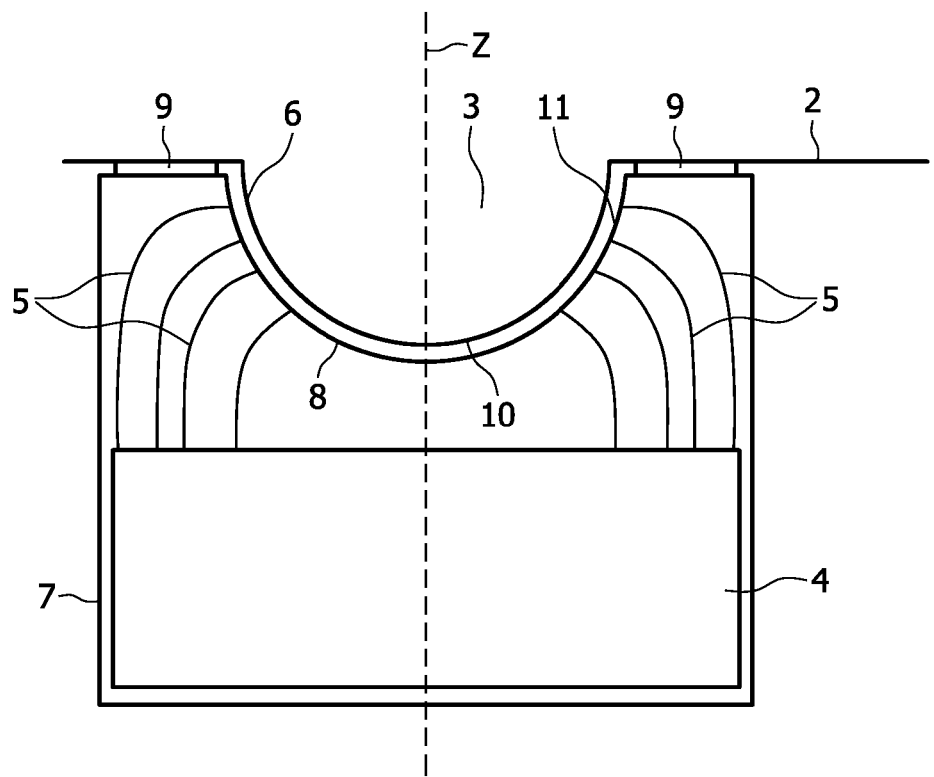
FIG. 2 schematically shows a portion in a region of the receptacle according to a first embodiment.

A first embodiment will now be described with respect to FIG. 2. In FIG. 2, only that portion of the device 1 for imaging the interior of turbid media is schematically shown where the receptacle 3 and the measurement system 4 are arranged.

In the embodiment, the receptacle 3 is mounted on the cradle 2. The receptacle 3 is made from a material having approximately the same optical properties as the optically matching fluid which is located between the turbid medium and the inner surface 6 of the receptacle 3. An example for such a material is polyoxymethylene (POM). Other suitable materials are for example nylon and other turbid plastics. Thus, the material of the receptacle 3 is capable of guiding light from the inner surface 6 of the receptacle 3 to the outer surface thereof and vice versa. In other words, the material of the receptacle 3 serves as a light guide.

The measurement system 4 and the light guides 5 connecting to the measurement system 4 are arranged in a movable member 7 which is movable with respect to the receptacle 3 and the cradle 2. In the embodiment, the movable member 7 can rotate about an axis of rotation Z with respect to the receptacle 3. The receptacle 3 has rotational symmetry and the axis of rotation Z is located in the rotational center of symmetry of the receptacle 3. On the side facing the receptacle 3, the movable member 7 is provided with a counterfitting part 8 the shape of which is adapted to the shape of the outer surface of the receptacle 3. The outer surface of the receptacle 3 forms a coupling surface 10, as will be described below. The size of the counterfitting part 8 is slightly larger than the size of the coupling surface 10 such that a small space remains in-between in order to allow rotational movement between the movable member 7 and the receptacle 3. A seal 9 surrounding the opening of the receptacle 3 is provided which seals the space between the counterfitting part 8 and the coupling surface 10 with respect to the exterior. The seal 9 is structured such that it allows rotation of the movable member 7 in relation to the receptacle 3 and the cradle 2.

As schematically indicated in FIG. 2, a plurality of light guides 5 extends from the measurement system 4 to the surface of the counterfitting part 8 facing the coupling surface 10. The surface of the counterfitting part 8 facing the coupling surface 10 forms a coupling member 11. In the present embodiment, the light guides 5 are formed by fibers capable of transmitting optical signals, such as e.g. glass fibers. One end of the respective light guides 5 ends at the surface of the counterfitting part 8 forming the coupling member 11. The space between the coupling surface 10 and the coupling member 11 is filled with an optically matching fluid which serves to provide optical coupling between the coupling surface 10 and the coupling member 11 and acts as a lubricant for the relative movement between the movable member 7 and the receptacle 3.

In operation, the light used for examination is transmitted from the light source to the coupling member 11 via one of the light guides 5, is transmitted from the coupling member 11 to the coupling surface 10, and is transmitted from the coupling surface 10 to the turbid medium placed in the receptacle 3 via the light guide formed by the material of the receptacle 3 and the optically matching medium contained in the receptacle 3. Further, the light emanating from the turbid medium is transmitted to the coupling surface 10 by means of the optically matching medium and the light guiding material of the receptacle 3, is transmitted from the coupling surface 10 to the coupling member 11, and is transmitted to the detectors via the light guides 5 in the movable member 7. After a measurement is performed, the movable member 7 is rotated relative to the receptacle 3 and further measurements are performed in different relative arrangements of the movable member 7 with respect to the receptacle 3. As a consequence, the coupling surface 10 and the coupling member 11 form an interface for transmitting light between the receptacle 3 and the measurement system 4. The coupling surface 10 acts as a first interface surface and the coupling member 11 acts as a second interface surface. Thus, an optical interface is provided, which allows relative movement between the measurement system 4 and the receptacle 3 and, at the same time, provides good optical coupling properties.

Throughout the scan, the light guides 5 connecting to the respective detectors have a fixed distance to the light guide 5 connecting to the light source, when the measurement system 4 is only rotated with respect to the receptacle 3. Thus, by pre-filtering or pre-amplifying it can be achieved that the light intensity for all detectors is in the same order of magnitude, making detector design and calibration easier.

Although it has been described that only one of the light guides 5 is used for transmitting light from the light source to the receptacle 3, a plurality of the light guides 5 may be used instead. If a plurality of light guides 5 is used for connecting to the light source during a scan, due to the rotational symmetry the source positions are located on several rings with respect to the receptacle 3. Thus, even in this case only a small fiber-switch is required, since one fiber can be used for each ring, i.e. for each plane perpendicular to the axis Z. Although the distance between source and detectors becomes again variable in this arrangement, the variability is still reduced compared to the prior art systems.

As a consequence, noise sensitivity of the sensors becomes less of an issue which allows using cheaper detectors. At the same time, boundary effects resulting from coupling light into and out of the turbid medium to be imaged are reduced, since the turbid medium is surrounded by an optically matching medium during the measurement.

Further, the receptacle 3 comprising the coupling surface 10 as its outer surface is structured such that it can be detached from the cradle 2 and replaced by another receptacle having a different size of the volume for accommodating the turbid medium. In other words, the receptacle 3 comprising the coupling surface 10 is provided as a replaceable, i.e. attachable and detachable, receptacle unit. Thus, the device 1 for imaging the interior of turbid media can be easily adapted to different sizes of turbid media without deteriorating the quality of the reconstructed image.

Second Embodiment

A second embodiment will now be described with respect to FIG. 3. In FIG. 3, again only that portion of the device 1 for imaging the interior of turbid media is schematically shown where the receptacle 103 and the measurement system 104 are arranged.

Figure 3:
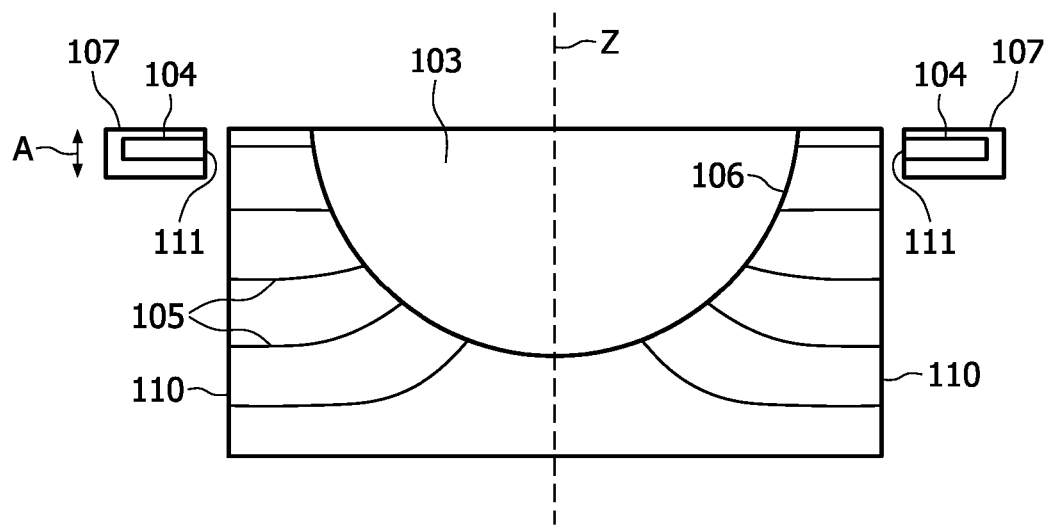
FIG. 3 schematically shows a portion in a region of the receptacle according to a second embodiment.

As can be seen in FIG. 3, the receptacle 103 according to the second embodiment forms a cavity having rotational symmetry with respect to an axis of rotation Z. Further, the receptacle has an outer surface which is formed in a cylindrical shape and has rotational symmetry with respect to the axis Z. The inner surface 106 of the receptacle 103 is provided with first ends of a plurality of light guides 105 optically connecting the inner surface 106 to the outer surface of the receptacle 103. The respective other ends of the light guides 105 end at the outer surface of the receptacle 103 which forms a coupling surface 110, as will be described below. The light guides 105 may be formed by light guiding fibers, for example. A plurality of such light guides 105 is distributed in the circumferential direction of the coupling surface 110 in a plane perpendicular to the axis Z.

In a position facing the coupling surface 110, a movable member 107 is arranged which is shaped as a ring surrounding the coupling surface 110. As can be seen in FIG. 3, a measurement system 104 is arranged in the movable member 107. The measurement system 104 comprises at least one light source and a plurality of detectors. Again, the light source can be preferably realized as a laser. The movable member 107 is constructed such that it can be rotated about the axis of rotation Z with respect to the receptacle 103. The surface of the movable member 107 facing the coupling surface 110 forms a coupling member 111. To this purpose, this surface of the movable member 107 may be either provided with the light source and the detectors or with appropriate light guides for guiding light from the light source to the coupling member 111 and for guiding light from the coupling member 111 to the respective detectors. Such light guides may be provided in form of light guiding fibers or lenses or in form of a combination of fibers and lenses, for example.

In operation, by rotating the movable member 107 to a specific orientation with respect to the receptacle 103, a specific one of the light guides 105 connecting the coupling surface 110 to the inner surface 106 of the receptacle 103 can be selected for illuminating the turbid medium. Other light guides 105 located on the same height on the coupling surface 110 can then be used for transmitting light emanating from the turbid medium to the detectors. By rotating the ring, different light guides 105 can then be used for connecting to the light source and to the detectors, respectively. The light coming from the light source is transmitted from the coupling member 111 to the coupling surface 110, from the coupling surface 110 via the light guide 105 to the inner surface 106 of the receptacle 103, and through the optically matching medium to the turbid medium. The light emanating from the turbid medium is transmitted through the optically matching medium, from the inner surface 106 to the coupling surface 110 via the light guides 105, from the coupling surface 110 to the coupling member 111, and then to the respective detectors. In this way, every light guide 105 can be used for injection of light and every light guide can be used as a detection position.

Further, as indicated by arrow A in FIG. 3, the movable member 107 is movable in the direction parallel to the axis of rotation Z. Thus, the light from the light source can be coupled to the turbid medium in different heights during a scan and the light emanating from the turbid medium can be detected in different heights. In this case, due to the rotational symmetry the source positions are located on several rings with respect to the receptacle 103.

The coupling surface 110 and the coupling member 111 form an interface for transmitting light between the receptacle 103 and the measurement system 104. The coupling surface 110 serves as first interface surface and the coupling member 111 serves as second interface surface. Thus, an optical interface is provided, which allows relative movement between the measurement system 104 and the receptacle 103 and, at the same time, provides good optical coupling properties. The coupling between the coupling surface 110 and the coupling member 111 may be realized as direct transmission from one light guide to another light guide, for example from fiber to fiber, or further optical elements such as lenses, mirrors, etc. may be interposed therebetween.

Also according to this embodiment, the advantages achieved by provision of an optically matching medium between the turbid medium and the receptacle 103 are maintained. Further, at least within a single ring the distance from the light source to the respective detectors is fixed during the scan and thus calibration of the detectors is facilitated and less expensive detectors can be used. Since the relative movement between the measurement system 104 and the receptacle 103 is allowed, only a reduced number of detectors is required which is advantageous under cost aspects.

Furthermore, in the second embodiment the receptacle 103 comprising the coupling surface 110 as an outer surface is provided as a removable insert which can be attached to and detached from the cradle 2. Thus, the receptacle 103 and the coupling surface 110 are provided as a removable receptacle unit. As a result, the device 1 for imaging the interior of turbid media can be easily adapted to different sizes of turbid media without deteriorating the quality of the reconstructed image by providing receptacle units having different sizes of volumes for accommodating turbid media.

Although the movable member 107 is formed as a complete ring surrounding the coupling surface 110 in the second embodiment, the movable member 107 may also be formed as only a part of a ring partially surrounding the coupling surface 110. Further, the movable member 107 may be a part of a larger rotating system extending below the receptacle 103. Further, the measurement system 104 does not have to be provided in the movable member 107 but may also be optically connected to the movable member 107 by means of light guides, for example by optically guiding fibers.

Although it has been described that the coupling surface 110 is formed by a cylindrical outer surface of the receptacle 103, a different construction may be implemented as well. Since the inner surface 106 is optically connected to the coupling surface 110 by light guides 105 provided in the material of the receptacle 103, the arrangement of the ends of the light guides 105 facing away from the turbid medium can be relatively freely designed. However, preferably these ends lead to a coupling surface having a circular circumference and the coupling member has a matching circular shape and the coupling surface and the coupling member can be rotated with respect to each other about a common axis of symmetry.

Although the provision of only one light source has been described with respect to the embodiments, a plurality of light sources may be provided instead. Multiple wavelengths can be used by multiplexing light from different light sources, for example from different lasers, into the light guide connecting to the light source.

From the inner surface of the receptacle to the coupling surface, the light is guided by a light guide. In the first embodiment the light is guided by the material of the receptacle. In the second embodiment the light is guided by fibers. Further, the light is guided from the light source to the coupling member and from the coupling member to the detectors via light guides. The coupling surface and the coupling member form an interface at which the light is coupled from the light guides connecting the coupling surface and the inner surface of the receptacle to the light guides connecting the coupling member and the light source and detectors, respectively.

The invention claimed is:

1. A device for imaging an interior of an optically turbid medium comprising:
   a receptacle configured to accommodate the optically turbid medium for examination and an optically matching medium filling a space between an inner surface of the receptacle and the optically turbid medium;
   at least one light source generating light to be coupled into the receptacle;
   at least one detector for detecting light emanating from the receptacle;
   a coupling surface optically coupled to the inner surface of the receptacle; and
   a coupling member optically coupled to the light source and the detector;
   wherein the coupling member is movable to a plurality of different positions relative to the coupling surface and configured to establish an optical connection from the light source to the inner surface of the receptacle and from the inner surface of the receptacle to the at least one detector in the plurality of different positions, and
   wherein an optically matching fluid is provided between the coupling member and the coupling surface for providing optical coupling between the coupling member and the coupling surface, and for acting as a lubricant for the relative movement between the coupling member and the coupling surface.

2. The device for imaging the interior of an optically turbid medium according to claim 1, wherein the coupling member is rotatably movable relative to the coupling surface about a rotational axis of symmetry (Z).

3. The device for imaging the interior of an optically turbid medium according to claim 1, wherein the coupling member is further linearly movable in the direction of the axis of symmetry (Z).

4. The device for imaging the interior of an optically turbid medium according to claim 1, wherein the coupling surface has a cylindrical shape.

5. The device for imaging the interior of an optically turbid medium according to claim 1, wherein the coupling surface is formed by an outer surface of the receptacle facing away from the turbid medium to be examined.

6. The device for imaging the interior of an optically turbid medium according to claim 1 wherein the receptacle is made from a material having optical properties the same as optical properties of the optically matching fluid.

7. The device for imaging the interior of an optically turbid medium according to claim 1 wherein the inner surface of the receptacle is coupled to the coupling surface by means of light guiding fibers.

8. The device for imaging the interior of an optically turbid medium according to claim 1, wherein the device comprises a receptacle unit comprising the receptacle and the coupling surface, the receptacle unit being attachable to and detachable from the device.

9. The device for imaging the interior of an optically turbid medium according to claim 1, wherein the device is a medical image acquisition device.

10. A device for imaging an interior of an optically turbid medium, the device comprising:
- a receptacle configured to accommodate an optically turbid medium for examination and an optically matching fluid filling a space between an inner surface of the receptacle and the optically turbid medium when attached to a cradle, an outer surface of the receptacle forming a coupling surface optically coupled to the inner surface of the receptacle; and
- a moveable member having counterfitting part configured to receive the coupling surface of the receptacle, an inner surface of the counterfitting part facing the coupling surface and forming a coupling member, the moveable member being configured to rotate relative to the receptacle for performing a plurality of measurements in different relative arrangements with respect to the receptacle, wherein the coupling surface and the coupling member are configured for coupling light from a light source optically coupled to the coupling member into the receptacle, and for coupling light emanating from the receptacle to a detector optically coupled to the coupling member, wherein the movable member comprises a plurality of light guides arranged between the coupling member and a measurement system comprising the detector, the light emanating from the receptacle being transmitted via at least one of the plurality of light guides, wherein a space between the coupling surface and the coupling member contains an optically matching fluid configured to provide optical coupling between the coupling surface and the coupling member and to act as a lubricant for the relative movement between the movable member and the receptacle.

* * * * *